(12) United States Patent
Nagano et al.

(10) Patent No.: US 7,087,766 B2
(45) Date of Patent: Aug. 8, 2006

(54) REAGENTS FOR THE QUANTITATION OF ACTIVE OXYGEN

(75) Inventors: Tetsuo Nagano, 1-28-15, Amanuma, Suginami-ku, Tokyo 167-0032 (JP); Yasuteru Urano, Kanagawa (JP); Ken-ichi Setsukinai, Tokyo (JP)

(73) Assignees: Daiichi Pure Chemicals Co., Ltd., Tokyo (JP); Tetsuo Nagano, Tokyo (JP)

( * ) Notice: Subject to any disclaimer, the term of this patent is extended or adjusted under 35 U.S.C. 154(b) by 419 days.

(21) Appl. No.: 10/204,417

(22) PCT Filed: Feb. 28, 2001

(86) PCT No.: PCT/JP01/01504

§ 371 (c)(1),
(2), (4) Date: Feb. 3, 2003

(87) PCT Pub. No.: WO01/64664

PCT Pub. Date: Sep. 7, 2001

(65) Prior Publication Data
US 2003/0153027 A1 Aug. 14, 2003

(30) Foreign Application Priority Data
Feb. 29, 2000 (JP) .............................. 2000-054557

(51) Int. Cl.
*C07D 311/02* (2006.01)
*C07D 311/78* (2006.01)
(52) U.S. Cl. .................... 549/223; 549/283
(58) Field of Classification Search .............. 549/223, 549/283
See application file for complete search history.

(56) References Cited

U.S. PATENT DOCUMENTS

| | | | |
|---|---|---|---|
| 5,623,080 A | 4/1997 | Neckers et al. | |
| 6,525,088 B1 | 2/2003 | Nagano et al. | |
| 6,903,226 B1 * | 6/2005 | Nagano et al. | 549/391 |

FOREIGN PATENT DOCUMENTS

| | | |
|---|---|---|
| EP | 0515133 | 11/1992 |
| JP | 60-54381 | 3/1985 |

OTHER PUBLICATIONS

Firth et al, J. Chem. Research, vol. 2000, No. 7, pp. 308-309, Jul. 2000.*
English Language Abstract of JP 60-54381.
Nagano, T., Free Radicals in Clinical Medicine, vol. 7, pp. 35-41, 1993.
Saito, I., et al., J. Am. Chem. Soc., vol. 107, pp. 6329-6334, 1985.
T. W. Greene et al., Protective Groups in Organic Synthesis, John Wiley & Sons, Inc., 1981, pp. v-xxi.
Kabatc, J., et al., Polymer 40(3), pp. 735-745 (1999).
Setsukinai, Ken-ichi, et al., J. Chem. Soc., Perkin Trans. 2, 12, pp. 2453-2457, 2000.
U.S. Appl. No. 10/204,418, filed Aug. 28, 2002 (National Stage of PCT/JP01/01502 filed Feb. 28, 2001) having the title "Method for Measurement by Using Long-Lived Excitation Fluorescence" (Applicants: Tetsuo Nagano et al).
U.S. Appl. No. 10/203,658, filed Aug. 27, 2002 (National Stage of PCT/JP01/01503 filed Feb. 28, 2001) having the title "Fluorescent Probe for Zinc" (Applicants: Tetsuo Nagano et al.).

* cited by examiner

Primary Examiner—Zinna N. Davis
(74) Attorney, Agent, or Firm—Greenblum & Bernstein, P.L.C.

(57) ABSTRACT

A compound represented by general formula (I) or (II) or a salt thereof and an agent for measurement of a reactive oxygen comprising said compound or a salt thereof:

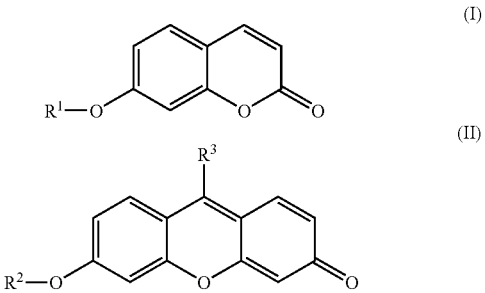

wherein $R^1$ and $R^2$ independently represent an aryl group which may be substituted, e.g., a phenyl group substituted with an amino group or a hydroxy group, and $R^3$ represents a 2-carboxyphenyl group which may be substituted.

18 Claims, 8 Drawing Sheets

REAGENTS FOR THE QUANTITATION OF ACTIVE OXYGEN

TECHNICAL FIELD

The present invention relates to a compound or a salt thereof useful as an agent for measurement of a reactive oxygen. The present invention also relates to an agent for measurement of a reactive oxygen comprising the aforementioned compound or a salt thereof.

BACKGROUND ART

It is known that, in living organisms and life phenomena, free radical species such as nitrogen monoxide act as a second messenger for signal transduction, and they exert various physiological functions, for example, control of blood pressure in the circulatory system and the like. Reactive oxygen, which is one type of free radical species, is a generic term for superoxide anion, hydrogen peroxide, hydroxyl radical, singlet oxygen and the like. Among them, superoxide anion and hydrogen peroxide have already been revealed to exert important physiological functions in the immune system and the like. There are also many articles reporting that hydroxyl radical has been found to be involved in vascular disorders or brain disorders after ischemia or DNA modification by ultraviolet, and the radical is considered to be a reactive oxygen species having particularly high harmful nature in relation to causes and pathologies of diseases. As for singlet oxygen, its role and the like has little been revealed so far. Recently, some evidence has been obtained suggesting that singlet oxygen is a reactive species in the photodynamic therapy, which is one of cancer therapies, and is generated by various kinds of oxidases, peroxidases and the like in living organisms, which suggests its role of important physiological functions.

Elucidation of the role of reactive oxygen species in living organisms has thus become more and more important. However, there are many problems in methods for measurement of the species. As for methods for measurement of hydroxyl radical, various reports have been made on its measurement by the electron spin resonance (ESR) method. However, the ESR method has fundamental difficulty of using living cells as measurement samples, and the measurement and the evaluation at an individual cell level are practically impossible. A method is also known in which DCFH-DA (2′,7′-dichlorodihydrofluorescein diacetate, Molecular Probes, catalog No. D-399), which is capable of measuring wide variety of reactive oxygen species, is used together with an inhibitor against generation of other reactive oxygen species, and hydroxyl radical is detected under a microscope. However, results obtained in the coexistence of the inhibitor includes some factors different from reactions in a living organism. In addition, DCFH-DA is very susceptible to autoxidation, and for this reason, background fluorescence by autoxidation interferes the detection when the same field is needed to be observed several times. The method is also very inconvenient from viewpoint of operability and storability as it requires operations in the dark.

Ten or more kinds of methods have been known as methods for measurement of singlet oxygen, including the chemiluminescence method, the ESR method, and the luminescence method. However, these methods in common give only low specificity and sensitivity, and thus they are not reliable methods (as for the method for specific detection of singlet oxygen, see, Nagano, T., et al., Free radicals in Clinical Medicine, Vol.7, pp.35–41, 1993 and the like). The DCFH-DA may be used in the measurement of singlet oxygen, however, problems of DCFH-DA, per se, cannot be avoided. Therefore, it has been desired to develop a method for measurement of singlet oxygen species, which can be used in research of reactive oxygen species and is excellent in specificity and sensitivity with easy operability.

DISCLOSURE OF THE INVENTION

An object of the present invention is to provide a compound useful as an agent for measurement of a reactive oxygen such as hydroxyl radical and singlet oxygen. Another object of the present invention is to provide an agent for measurement of a reactive oxygen comprising said compound, and to provide a method for measurement of a reactive oxygen using said compound. More specifically, the object of the present invention is to provide an agent for accurately and conveniently measuring a reactive oxygen that are localized in a particular class of cells or tissues in a living organism by a bioimaging technique.

The inventors of the present invention conducted various studies to achieve the foregoing objects. As a result, they succeeded in providing an agent for specifically detecting singlet oxygen (International Publication WO 99/51586). The inventors further conducted researches, and found that a substantially non-fluorescent compound represented by general formula (I) or (II) is efficiently reacted with a reactive oxygen under physiological conditions to give a dearylated fluorescent compound, and that a reactive oxygen can be measured with very high specificity and sensitivity by using the compound represented by the general formula (I) or (II) as an agent for measurement of hydroxyl radical or singlet oxygen to measure the fluorescence of the dearylated compound generated upon the reaction with a reactive oxygen which are localized in living cells or living tissues. They also found that the compound represented by the general formula (I) or (II) is not absolutely affected by autoxidation. The present invention was achieved on the basis of these findings.

The present invention thus provides a compound represented by general formula (I) or (II) or a salt thereof:

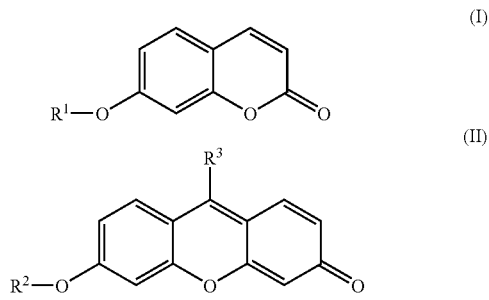

wherein $R^1$ and $R^2$ independently represent an aryl group which may be substituted and $R^3$ represents a 2-carboxyphenyl group which may be substituted. According to preferred embodiments of the present invention, provided are the aforementioned compound or a salt thereof in which $R^1$ and $R^2$ represent a phenyl group substituted with an amino group or a hydroxy group; and the aforementioned compound or a salt thereof in which $R^3$ is a 2-carboxyphenyl group.

From another aspect of the present invention, an agent for measurement of a reactive oxygen is provided which comprises the compound represented by the general formula (I)

or (II) or a salt thereof. The present invention further provides a method for measurement of a reactive oxygen which comprises the steps of: (A) reacting the compound represented by the general formula (I) or (II) or a salt thereof with a reactive oxygen; and (B) measuring fluorescence of a dearylated compound or a salt thereof generated in the above step (A) (a compound represented by the general formula (I) in which $R^1$ is a hydrogen atom or a compound represented by general formula (II) in which $R^2$ is a hydrogen atom).

BEST MODE FOR CARRYING OUT THE INVENTION

Figure 1:
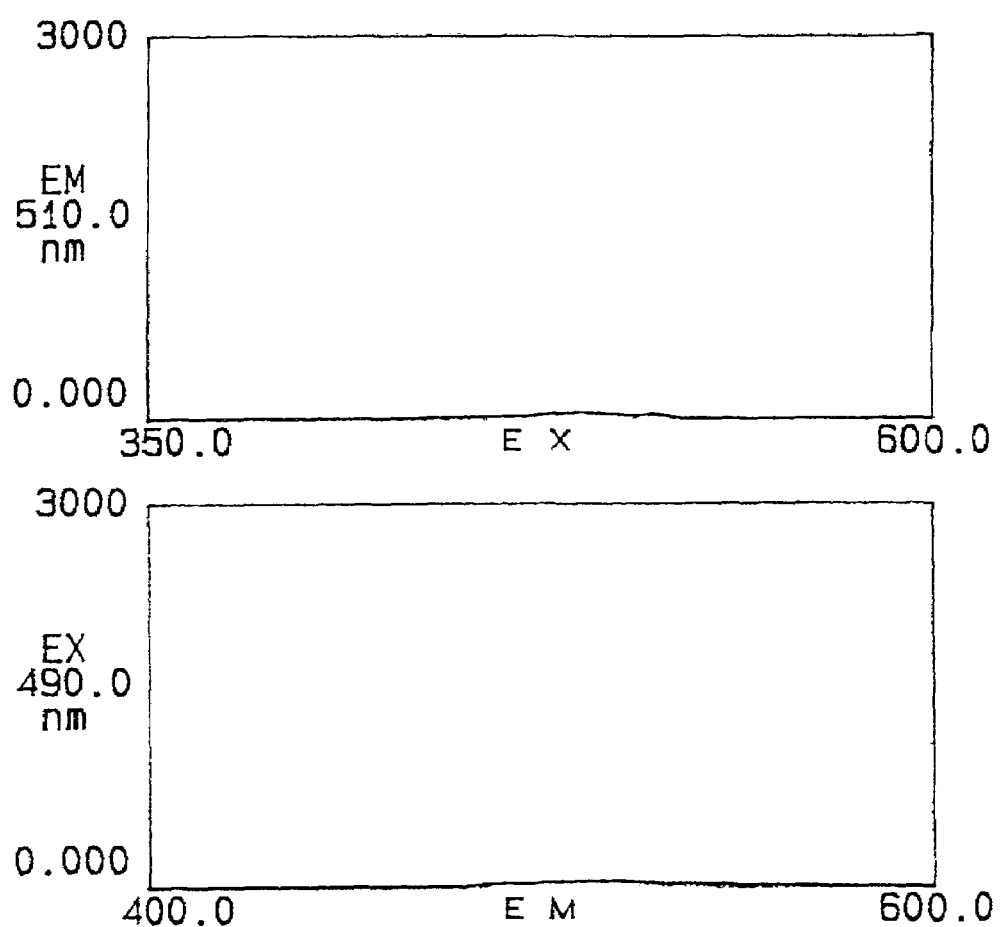
FIG. 1 shows an excitation spectrum and a fluorescence spectrum of a 10 µM solution of the compound (ss-3F) of the present invention obtained in Example 3.

All disclosures in the specification and claims of Japanese Patent Application No. 2000-54557 are incorporated herein by reference.

As the aryl group represented by $R^1$ or $R^2$, for example, a monocyclic, bicyclic, or tricyclic aryl group having about 6 to 14 ring-constituting atoms can be used. Preferably a phenyl group or a naphthyl group, and more preferably a phenyl group can be used. The aryl group may have one or more substituents on the ring. When the aryl group has two or more substituents, they may be the same or different. The type and substituting position of the substituent are not particularly limited. For example, a $C_{1-6}$ alkyl group (the alkyl group may be any of linear, branched, cyclic, or a combination thereof, and the same shall apply to an alkyl moiety of other substituents having the alkyl moiety), a $C_{1-6}$ haloalkyl group, a $C_{1-6}$ alkenyl group, a $C_{1-6}$ alkoxy group, a halogen atom (the halogen atom may be any of a fluorine atom, a chlorine atom, a bromine atom, or an iodine atom), a cyano group, a nitro group, an optionally substituted amino group, a carboxyl group, an alkoxycarbonyl group, a $C_{1-6}$ alkanoyl group, a $C_{1-6}$ haloalkanoyl group, an aroyl group, a hydroxy group, an alkylenedioxy group or the like may be used as the substituent.

$R^1$ or $R^2$ is preferably a substituted phenyl group and a monosubstituted phenyl group is more preferable. As the monosubstituted phenyl group, a phenyl group having non-substituted amino group or a hydroxy group is particularly preferred. A substituting position of the substituent is preferably in ortho-position or para-position. A benzene ring of a 2-carboxyphenyl group represented by $R^3$ may have one or more substituents. When the benzene ring has two or more substituents, they may be the same or different. The group explained for the aforementioned aryl group can be used as a substituent on the benzene ring, and $R^3$ is preferably a non-substituted 2-carboxyphenyl group.

The compound represented by the general formula (I) or (II) can exist as a salt. Examples of salts include a base addition salt, an acid addition salt, and an amino acid salt. Examples of the base addition salts include: metal salts such as sodium salts, potassium salts, calcium salts, and magnesium salts; ammonium salts; and organic amine salts such as triethylamine salts, piperidine salts, and morpholine salts. Examples of the acid addition salts include: mineral acid salts such as hydrochlorides, sulfates, and nitrates; and organic acid salts such as methanesulfonates, p-toluenesulfonates, citrates, and oxalates. Examples of the amino acid salts include glycine salts. However, salts of the compounds of the present invention are not limited to these examples.

Among them, physiologically acceptable water-soluble salts can be suitably used for the agent and the measuring method of the present invention. Further, the compound represented by the general formula (I) or (II) in a free form or a salt thereof may exist as a hydrate or a solvate; and any of these substances fall within the scope of the present invention. The types of solvents that form the solvates are not particularly limited. For example, solvents such as ethanol, acetone, and isopropanol can be exemplified.

The compound represented by general formula (I) or (II) may have one or more asymmetric carbons depending on the type of the substituent, and stereoisomers such as optical isomers or diastereoisomers may exist. These stereoisomers in pure forms, any mixtures of these stereoisomers, racemates and the like fall within the scope of the present invention. In addition, the compound represented by formula (II) of the present invention may form a lactone ring in the molecule. It should be recognized that the compounds in which a lactone ring is formed also fall within the scope of the present invention. Optically active substances due to the aforementioned lactone formation also fall within the scope of the present invention.

The compound of the present invention represented by the general formula (I) or (II) can be prepared generally by arylating a corresponding coumarin compound (a compound represented by the general formula (I) in which $R^1$ is a hydrogen atom) or a fluorescein compound (a compound represented by the general formula (II) in which $R^2$ is a hydrogen atom). In general, an alkali metal salt of a coumarin compound or a fluorescein compound is prepared beforehand, and then the salt is reacted with an aryl iodide compound in a suitable solvent in the presence of cuprous chloride. Methods for preparation of typical compounds represented by the general formula (I) or (II) of the present invention are shown in the following schemes. The preparation methods shown in the schemes are more specifically detailed in Examples of the specification. Accordingly, one of ordinary skill in the art can prepare any compounds according to the present invention by suitably choosing a starting material and a reagent based on the explanations in the Examples and appropriately altering or modifying reaction conditions and steps, if necessary.

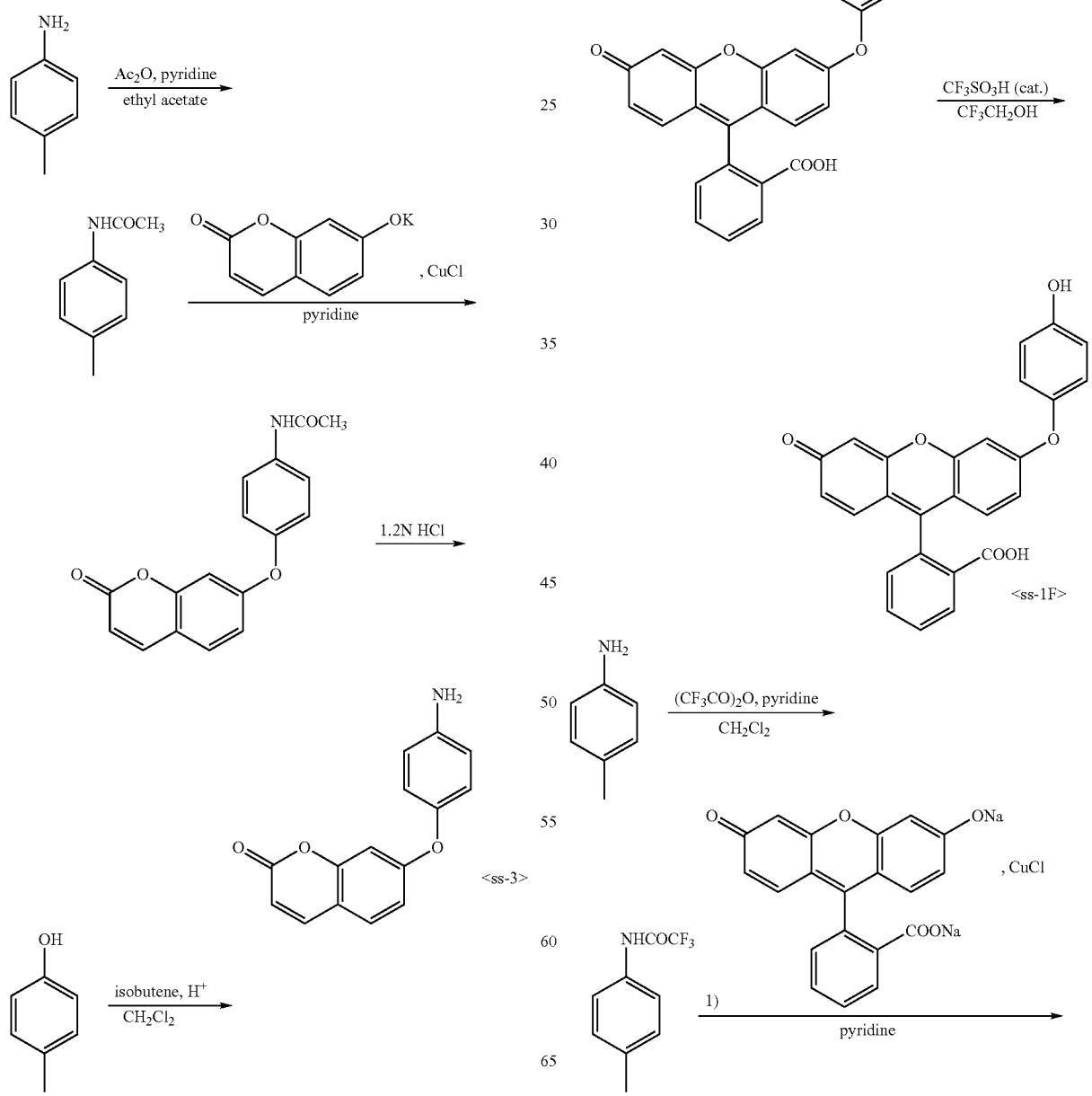

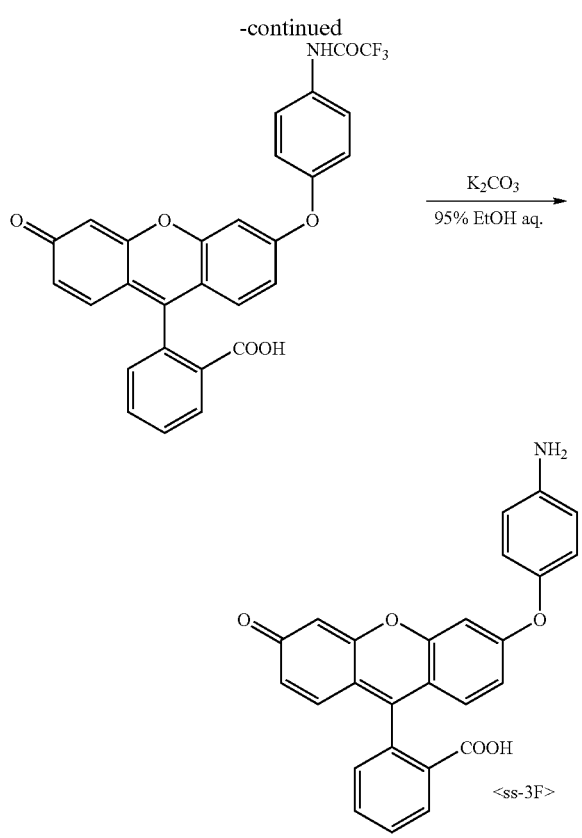

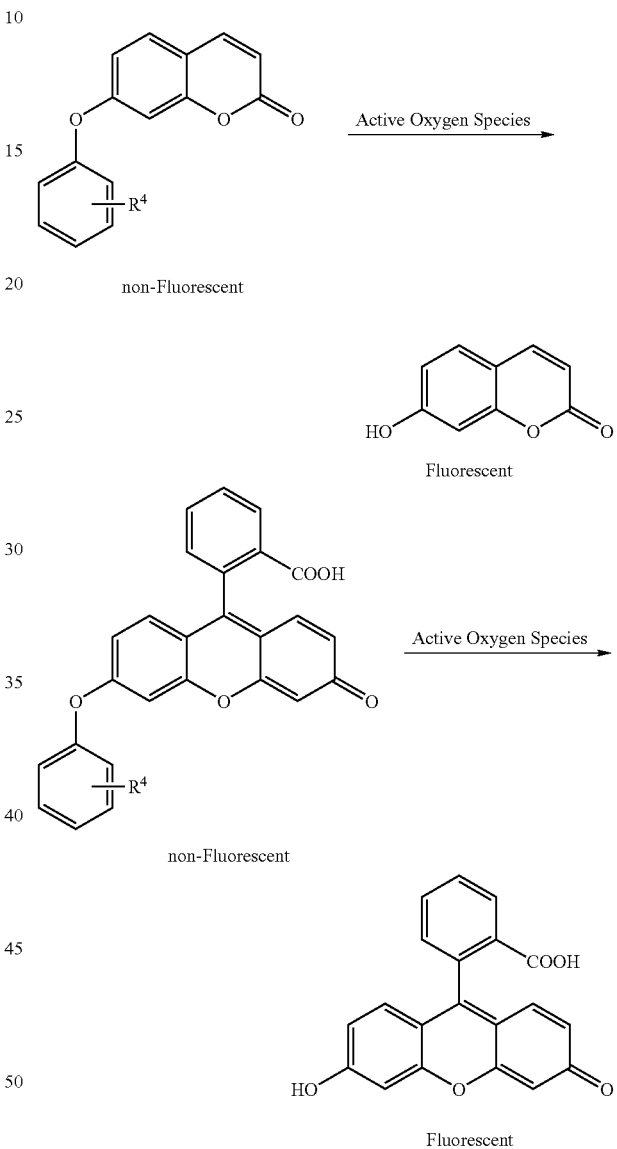

A target compound can sometimes be efficiently prepared by performing the reaction by optionally protecting a particular class of functional group in the reaction steps. Detailed explanations of protective groups are given in, for example, Protective Groups in Organic Synthesis, T. W. Greene, John Wiley & Sons, Inc., 1981, and therefore, one of ordinary skill in the art can choose suitable protective groups.

In the above preparations, isolation and purification of the products can be performed by an appropriate combination of techniques used in the field of organic synthesis, for example, filtration, extraction, washing, dehydration, concentration, crystallization, various chromatography techniques and the like. The synthetic intermediates in the aforementioned steps can be used for the subsequent reaction without particular purification. Where a salt of the compound of the present invention is prepared, when a salt of each compound is obtained in the above preparation method, the resulting salt, per se, may be purified. When a compound in a free form is obtained, the compound in a free form can be dissolved or suspended in a suitable solvent and then added with a base to form a salt, and the resulting salt may be purified, if necessary.

The compound of the present invention represented by the general formula (I) or (II) or a salt thereof has a property that it reacts with a reactive oxygen under a mild condition, for example, a physiological condition, to give a dearylated coumarin compound (corresponding to a compound represented by general formula (I) in which $R^1$ is a hydrogen atom) or a fluorescein compound (corresponding to a compound represented by general formula (II) in which $R^2$ is a hydrogen atom) or a salt thereof. The compound represented by the general formula (I) or (II) or a salt thereof is substantially non-fluorescent, whereas the dearylated coumarin compound or the fluorescein compound or a salt thereof has a property of emitting fluorescence with high intensity. Therefore, by subjecting a compound represented by the general formula (I) or (II) or a salt thereof to react with a reactive oxygen, and then measuring fluorescence of the dearylated compound or a salt thereof, the reactive oxygen can be measured selectively with high sensitivity.

(in the scheme, $R^4$ represents a p-amino group, an o-amino group, a p-hydroxy group, an o-hydroxy group and the like, and the reactive oxygen species is singlet oxygen, hydroxyl radical or the like.)

The types of reactive oxygens which are measurable by the agent of the present invention are not particularly limited. For example, any of superoxide anion, hydroxyl radical, singlet oxygen, and hydrogen peroxide can be measured. In particular, singlet oxygen and hydroxyl radical can be measured with high sensitivity and selectivity. For example, when the compound represented by general formula (I) or (II) or a salt thereof is used as an agent for measurement of a reactive oxygen, reactive oxygens localized in an individual cell or a particular class of tissue can be accurately and conveniently measured.

The term "measurement" used in the present specification should be construed in its broadest sense, including determinations, tests, and detections performed for the purpose of quantification, qualification, diagnosis or the like. The method for measuring a reactive oxygen of the present invention generally comprises the steps of: (A) reacting a compound represented by the general formula (I) or (II) or a salt thereof with a reactive oxygen; and (B) measuring fluorescence of a dearylated compound or a salt thereof produced in the above step (A) (corresponding to a compound represented by general formula (I) in which $R^1$ is a hydrogen atom or a compound represented by general formula (II) in which $R^2$ is a hydrogen atom).

The fluorescence of the dearylated compound or a salt thereof may be measured by a conventional method. A method for measurement of a fluorescence spectrum in vitro, a method for measurement of a fluorescence spectrum in vivo by a bioimaging technique and the like may be employed. For example, when quantification is performed, it is preferred to prepare a calibration curve beforehand according to a conventional method. As a quantitative hydroxyl radical generation system, for example, a gamma-radiolysis method can be used. As a singlet oxygen generation system, for example, the naphthalene endoperoxide system (Saito, I, .et al., J. Am. Chem. Soc., 107, pp. 6329–6334, 1985) can be used. The agent of the present invention has a property to be taken up intracellularly, and accordingly, the agent enables measurement of reactive oxygens localized in individual cells with high sensitivity by a bioimaging technique.

From another aspect of features of the compound of the present invention or a salt thereof, said compound or a salt thereof can specifically measure activity of an enzyme such as peroxidase, in which enzymatic reaction a reactive oxygen involves. Accordingly, the agent comprising the compound of the present invention or a salt thereof is useful as an agent for measurement of activity of an enzyme such as a peroxidase in which reaction a reactive oxygen involves.

The compound represented by the general formula (I) or (II) or a salt thereof, per se, may be used as the agent for measurement of a reactive oxygen of the present invention. If necessary, a composition may be used which is formulated with additives commonly used for preparation of a reagent. For example, additives such as solubilizers, pH adjusters, buffers, and isotonic agents can be used as additives for use of the agent in a physiological condition, and amounts of these additives can be suitably chosen by one of ordinary skill in the art. The compositions may be provided as compositions in appropriate forms, for example, powdery mixtures, lyophilized products, granules, tablets, solutions and the like.

EXAMPLES

The present invention will be more specifically explained by way of examples. However, the scope of the present invention is not limited to these examples.

Example 1

Synthesis of ss-3 (a Compound Represented by General Formula (I) in Which $R^1$ is a p-aminophenyl Group)

1) Synthesis of 4-Iodoacetanilide

4-Iodoaniline (11.0 g, 50.4 mmol) was dissolved in 60 mL of ethyl acetate and the solution was added with 10 mL of acetic anhydride (10.8 g, 106 mmol) and 7.8 mL of pyridine (7.65 g, 99.4 mmol), and the mixture was stirred at room temperature for 2 hours with an equipment of a $CaCl_2$ tube. A solvent was evaporated under reduced pressure to obtain 4-iodoacetanilide (yield: 13.0 g, percent yield: 99.0%).

m.p.: 174.5 to 175.5° C.

$^1$H-NMR (300 MHz Acetone-$d_6$); δ 2.04 (s, 3H), 7.46 (dd, J=9.0 Hz, 2.2 Hz, 1H), 7.60 (dd, J=9.0 Hz, 2.2 Hz, 1H), 9.21(br, 1H)

EI Mass $(M)^+$=261

2) Synthesis of pre ss-3 (Acetyl)

Potassium t-butoxide (123 mg, 1.10 mmol) was dissolved in a mixed solvent of 8 mL of benzene and 3 mL of methanol. The solution was then added with 7-hydroxycoumarin (196 mg, 1.21 mmol) and stirred for dissolution. The solvent was then removed by evaporation under reduced pressure to obtain a 7-hydroxycoumarin potassium salt. A solution of 4-iodoacetanilide (1.11 g, 4.26 m mol) dissolved in 12 mL of pyridine and cuprous chloride (124 mg, 1.25 mmol) were added to a 25 mL eggplant-type flask containing the 7-hydroxycoumarin potassium salt, and the mixture was heated under reflux under argon stream for 9 hours and 45 minutes. After stand for cooling to room temperature, the reaction mixture was added with 55 mL of water and then acidified with the addition of concentrated hydrochloric acid. The mixture was extracted with ethyl acetate (75 mL×4), and the combined organic layer was washed with saturated brine and dried over $Na_2SO_4$, and then the solvent was evaporated under reduced pressure. The residue was purified by column chromatography on silica gel (repeated twice using ethyl acetate as a sole eluent for both times) to obtain pre ss-3 (acetyl) as a yellow crystal (yield: 68.7 mg, percent yield: 21.2%).

m.p.: 197.0 to 199.0° C.

$^1$H-NMR (300 MHz Acetone-$d_6$); δ 2.08 (s, 3H), 6.27 (d, J=9.5 Hz, 1H), 6.79 (d, J=2.4 Hz, 1H), 6.92 (dd, J=8.6 Hz, 2.4 Hz, 1H), 7.09 (d, J=9.0 Hz, 2H), 7.65 (d, J=8.6 Hz, 1H), 7.74 (d, J=9.0 Hz, 2H), 7.93 (d, J=9.5 Hz, 1H)

EI Mass $(M)^+$=295

3) Synthesis of ss-3

Pre ss-3 (acetyl) (67 mg, 0.227 mmol) was added to 20 mL of 1.2 normal hydrochloric acid, and the reaction system was completely sealed and heated under reflux for 3 hours, and then stirred at room temperature for 1 hour and 30 minutes. The reaction mixture was added with an aqueous solution of saturated sodium hydrogencarbonate (65 mL) and extracted with ethyl acetate (75 mL×4). The organic layer was washed with saturated brine, dried over $Na_2SO_4$, and the solvent was then evaporated under reduced pressure. The residue was purified by column chromatography on silica gel (eluent; dichloromethane/ethyl acetate=3/1) to obtain ss-3 as a yellow crystal (yield: 38.0 mg, percent yield: 66.2%).

m.p.: 132.5 to 133.5° C.

$^1$H-NMR (300 MHz Acetone-$d_6$); δ 4.57 (br, 2H), 6.10 (d, J=9.5 Hz, 1H), 6.60–6.78 (m, 5H), 7.47 (d, J=8.6 Hz, 1H), 7.77 (d, J=9.5 Hz, 1H)

EI Mass $(M)^+$=253

Example 2

Synthesis of ss-1F (a Compound Represented by General Formula (II) in which $R^2$ is a p-hydroxyphenyl Group and $R^3$ is a 2-carboxyphenyl Group)

1) Synthesis of 4-tert-butoxyiodobenzene

4-Iodophenol (18.7 g, 85.1 mmol) was dissolved in 150 mL of dichloromethane and the solution was bubbled with isobutene until saturation under ice cooling. The mixture was then added with 10 drops of concentrated sulfuric acid and stirred at room temperature overnight. The reaction mixture was washed twice with a 50 ml aqueous solution of 2 normal sodium hydroxide, and the organic layer was dried over $Na_2SO_4$, and the solvent was evaporated under reduced pressure to obtain 4-tert-butoxyiodobenzene as a white crystal (yield: 16.6 g, percent yield: 70.7%).

m.p.: 40.0 to 41.5° C.
$^1$H-NMR (300 MHz $CDCl_3$); δ 1.33 (s, 9H), 6.75 (dd, J=9.0 Hz, 2.4 Hz, 2H), 7.55 (dd, J=9.0 Hz, 2.4 Hz, 2H)
EI Mass $(M)^+$=276

2) Synthesis of pre ss-1F (t-butyl)

Sodium fluorescein (3.75 g, 9.97 mmol), cuprous chloride (3.92 g, 39.6 mmol), and 4-tert-butoxyiodobenzene (8.05 g, 29.2 mmol) were added to 50 ml of pyridine, and the mixture was heated under reflux under argon stream for 10 hours and 15 minutes. The mixture was added with water (50 ml) and 80 ml of concentrated hydrochloric acid and extracted with dichloromethane. The organic layer was washed with saturated brine, dried over anhydrous $Na_2SO_4$, and then concentrated under reduced pressure. The residue was purified by column chromatography on silica gel (eluent: ethyl acetate/n-hexane=1/1) to obtain pre ss-1F (t-butyl) as a yellow solid (yield: 19.6 mg, percent yield: 0.4%).

m.p.: 136.0 to 138.0° C.
$^1$H-NMR (300 MHz CD3CN); δ 1.33 (s, 9H), 6.62–6.82 (m, 6H), 7.06 (m, 4H), 7.30 (d, J=7.5 Hz, 1H), 7.71–7.83 (m, 2H), 7.98 (d, J=6.4 Hz, 1H)
FAB Mass $(M+1)^+$=481

3) Synthesis of ss-1F

Pre ss-1F (t-butyl) (9.8 mg, 20.4 μmol) was dissolved in 10 mL of 2,2,2-trifluoroethanol, and the solution was added with 5 drops of a dilute solution of trifluoromethanesulfonic acid under ice cooling, and then the mixture was stirred under argon stream for 25 minutes under ice cooling. After the completion of the reaction, the reaction mixture was added with 40 mL of dichloromethane and washed twice with water and then with saturated brine, dried over $Na_2SO_4$. Then the solvent was evaporated under reduced pressure to obtain ss-1F as a yellow crystal (yield: 6.6 mg, percent yield: 76.9%).

m.p.: 127.0 to 129.0° C.
$^1$H-NMR (300 MHz Acetone-$d_6$); δ 6.48–6.67 (m, 6H), 6.79 (d, J=9.0 Hz, 2H), 6.87 (d, J=9.0 Hz, 2H), 7.17 (d, J=7.5 Hz, 1H), 7.58–7.71 (m, 2H), 7.86 (d, J=7.5 Hz, 1H)
FAB Mass $(M+1)^+$=425

Example 3

Synthesis of ss-3F (a Compound Represented by General Formula (II) in which $R^2$ is a p-aminophenyl Group and $R^3$ is a 2-carboxyphenyl Group)

1) Synthesis of 4-iodotrifluoroacetanilide

Trifluoroacetic anhydride (36.0 ml, 216 mmol, 45.0 g) and pyridine (17.0 ml, 210 mmol, 16.6 g) were added to a solution of 4-iodoaniline (25.0 g, 114 mmol) in 100 ml of dichloromethane under ice cooling, and the mixture was stirred under ice cooling until fuming and heat evolution were terminated. The mixture was then immediately returned to room temperature and continuously stirred for 19 hours. After the solvent was evaporated under reduced pressure, the residue was purified by chromatography on silica gel (eluent: ethyl acetate) to obtain 4-iodotrifluoroacetanilide as a light brown solid (yield: 34.1 g, percent yield: 94.8%).

m.p.: 148.5 to 149.0° C.
$^1$H-NMR (300 MHz, $CDCl_3$/TMS); d 7.35 (d, J=8.8 Hz, 2H), 7.71 (d, J=8.8 Hz, 1H), 7.90 (br, 1H)
EI Mass $(M)^+$=315

2) Synthesis of N'-trifluoroacetyl-ss-3F (TFA Salt)

Sodium fluorescein (3.77 g, 10.0 mmol) was dissolved in 50 ml of dimethylacetamide, and the mixture was stirred for 20 minutes. The mixture was added with a solution of 4-iodotrifluoroacetanilide (12.8 g, 4.05 mmol) in 60 ml of pyridine, and then added further with cuprous chloride (2.55 g, 25.8 mmol) and heated under reflux under argon stream for 9 hours. After the reaction mixture was cooled to room temperature, the mixture was added with 100 ml of water and further with 65 ml of concentrated hydrochloric acid for acidification. The mixture was extracted three times with ethyl acetate, and the combined organic layer was washed with saturated brine. The organic layer was then dried over sodium sulfate and the solvent was evaporated under reduced pressure. The residue was purified by chromatography on silica gel (eluent: ethyl acetate/n-hexane=1/1) to obtain pre ss-3F (TFA) as a yellow solid (yield: 76.6 mg, percent yield: 1.48%).

m.p.: 116.5–118.5° C.
$^1$H-NMR (300 MHz, DMSO-$d_6$); d 6.57–6.87 (m, 6H), 7.18 (d, J=9.0 Hz, 2H), 7.30 (d, J=7.5 Hz, 1H), 7.70–7.82 (m, 4H), 8.00 (d, J=7.5 Hz, 1H)
FAB Mass $(M+1)^+$=520

3) Synthesis of ss-3F

Pre ss-3F (TFA) (76.6 mg, 0.148 mmol) and anhydrous potassium carbonate (90.3 mg) were dissolved in a mixed solution of 20 ml of ethanol and 1.2 ml of water, and the mixture was heated under reflux for 4 hours. After the solution was cooled to room temperature, ethanol and water were evaporated under reduced pressure. The residue was added with water (20 ml) and then with 10 ml of 2N hydrochloric acid for acidification (pH 1). The mixture was extracted twice with dichloromethane, and the organic layers were combined and the solvent was evaporated under reduced pressure. The residue was purified by chromatography on silica gel (eluent: ethyl acetate/n-hexane=1/1) to obtain ss-3F as a yellow solid (yield: 13.6 mg, percent yield: 21.8%).

m.p.: 153.5 to 155.0° C.
$^1$H-NMR (300 MHz, acetone-$d_6$); d 6.60–6.89 (m, 10H), 7.29 (d, J=7.5 Hz, 1H), 7.72 (td, J=7.5 Hz, 1.5 Hz, 1H), 7.80 (td, J=7.5 Hz, 1.5 Hz, 1H), 7.98 (d, J=7.5 Hz, 1H)
FAB Mass $(M+1)^+$=424

Example 4

1) Fluorescence Spectrum ss-3F obtained in Example 3 was dissolved in DMF to a concentration of 10 mM, and then the solution was added with a 100 mM sodium phosphate buffer (pH 7.4) for dissolution at a final concentration of 10 μM. The excitation spectrum and the fluorescence spectrum of the 10 μM ss-3F solution were measured using a fluorophotometer F4500 (manufactured by Hitachi, Ltd.). Slit width was 2.5 nm for both the excitation spectrum and the fluorescence spectrum, and the photomultiplier voltage was 950 V. Measurement was carried out at the excitation wavelength of 490 nm and the fluorescence wavelength of 510 nm unless otherwise specified. The results are shown in FIG. 1. As clearly shown in FIG. 1, ss-3F, per se, emits no fluorescence.

Figure 2:
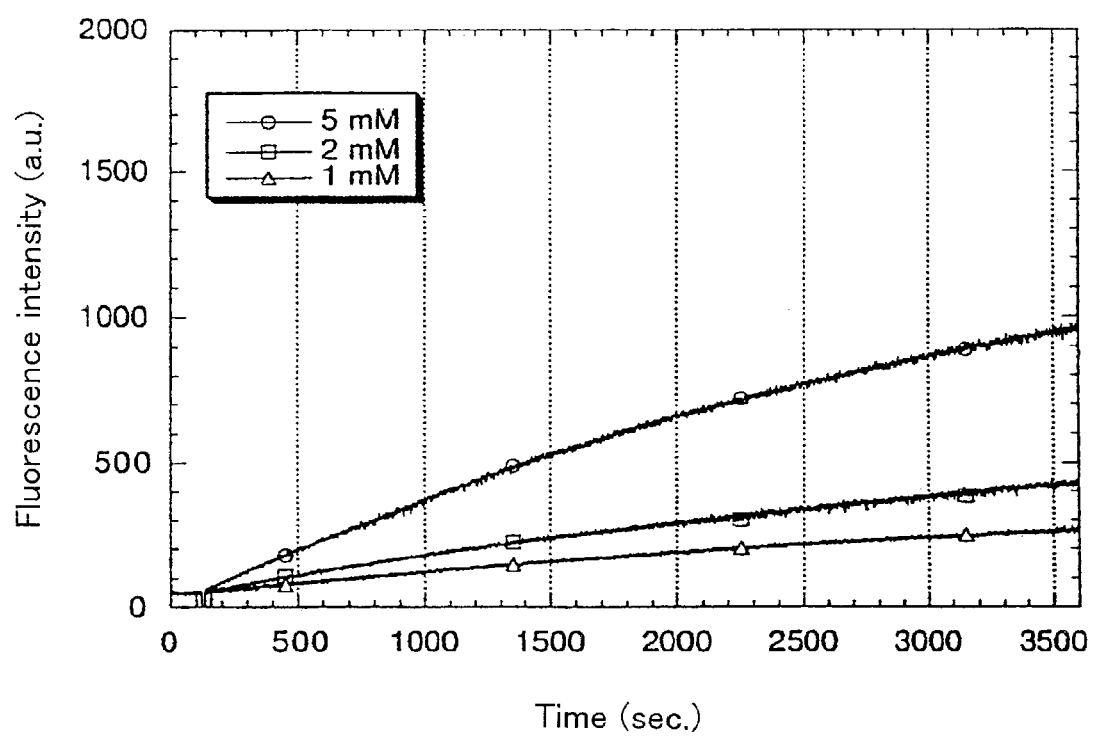
FIG. 2 shows results of measurements of changes in fluorescence intensity with time where a singlet oxygen generation system, i.e., EP-1, was added to a 10 µM solution of the compound (ss-3F) of the present invention obtained in Example 3.
Figure 3:
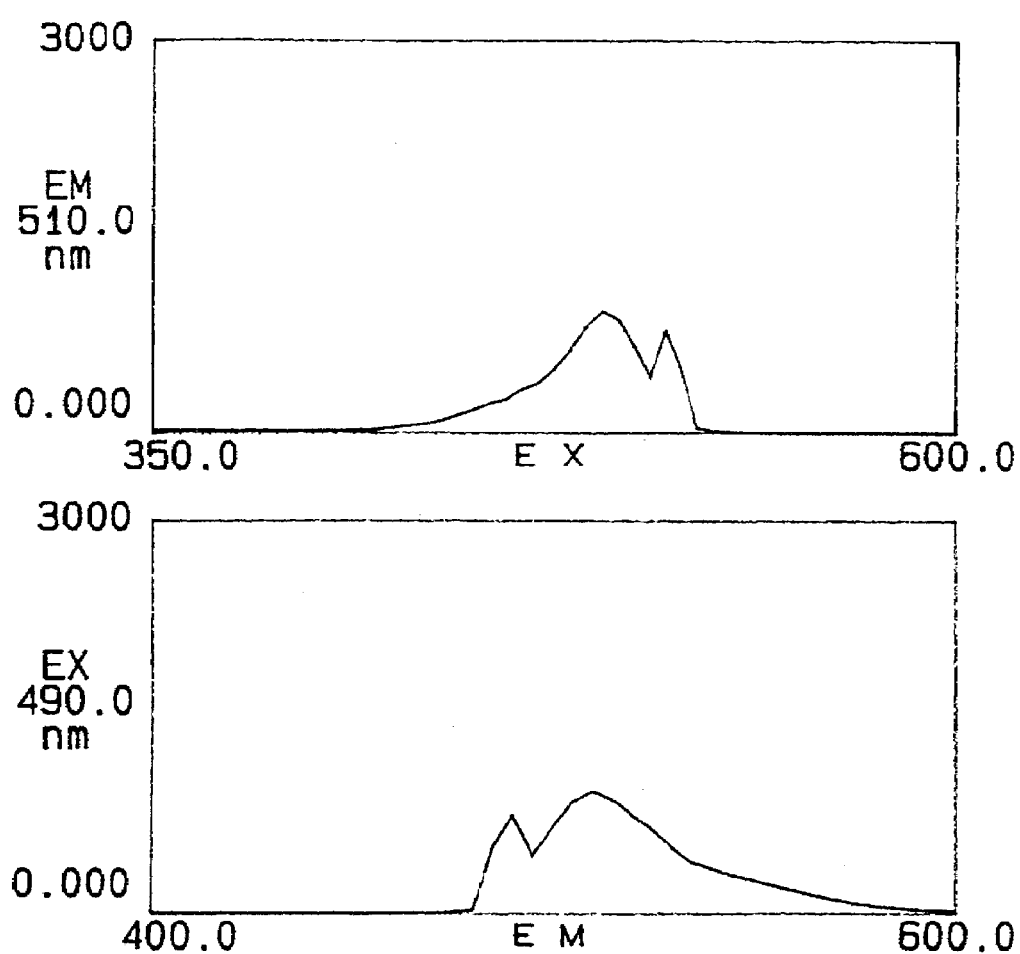
FIG. 3 shows an excitation spectrum and a fluorescence spectrum of the solution after the completion of the reaction shown in FIG. 2.

Subsequently, in order to investigate the reaction between ss-3F and singlet oxygen, a solution of EP-1 (a singlet oxygen generation system, i.e., the naphthalene endoperoxide compound; Saito, I, .et al., J. Am. Chem. Soc., 107, pp. 6329–6334, 1985) in dimethylformamide (DMF) was added to the 10 μM ss-3F solution to final concentrations of 1 mM, 2 mM, and 5 mM, and changes in fluorescence intensity with time was measured (EP-1 system). The temperature of the solution at this time was at 37° C. The results are shown in FIG. 2. The excitation spectrum and the fluorescence spectrum of the solution after the completion of the reaction were measured under the same conditions as described above. The results are shown in FIG. 3. As clearly shown in FIG. 2, when ss-3F and EP-1 were allowed to coexist, increase in fluorescence intensity was observed dependently on EP-1 concentrations as well as in time dependent manner. Also in FIG. 3, generation of fluorescence was observed, and it was verified that ss-3F generated fluorescence upon reaction with singlet oxygen.

Figure 4:
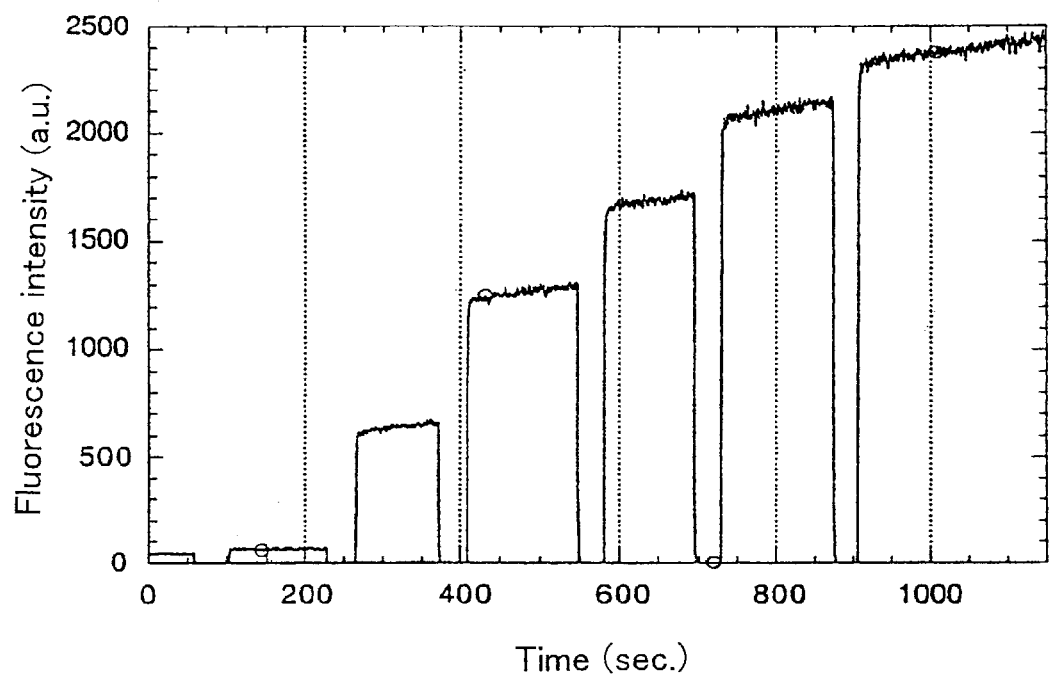
FIG. 4 shows results of measurements of changes in fluorescence intensity with time where a hydroxyl radical generation system, i.e., hydrogen peroxide and ferrous perchlorate, was added to a 10 µM solution of the compound (ss-3F) of the present invention obtained in Example 3.

Further, to investigate the reaction between ss-3F and hydroxyl radical, hydrogen peroxide was added to the 10 μM ss-3F solution to a final concentration of 1 mM, and then the mixture was added with ferrous perchlorate to a final concentration of 100 μM for each addition (5 times in total) to measure changes in fluorescence intensity with time (Fenton system). The results are shown in FIG. 4. As shown in FIG. 4, increase in fluorescence intensity was observed at each time of the addition of ferrous perchlorate, which verified that ss-3F emitted fluorescence upon reaction with hydroxyl radical.

Figure 5:
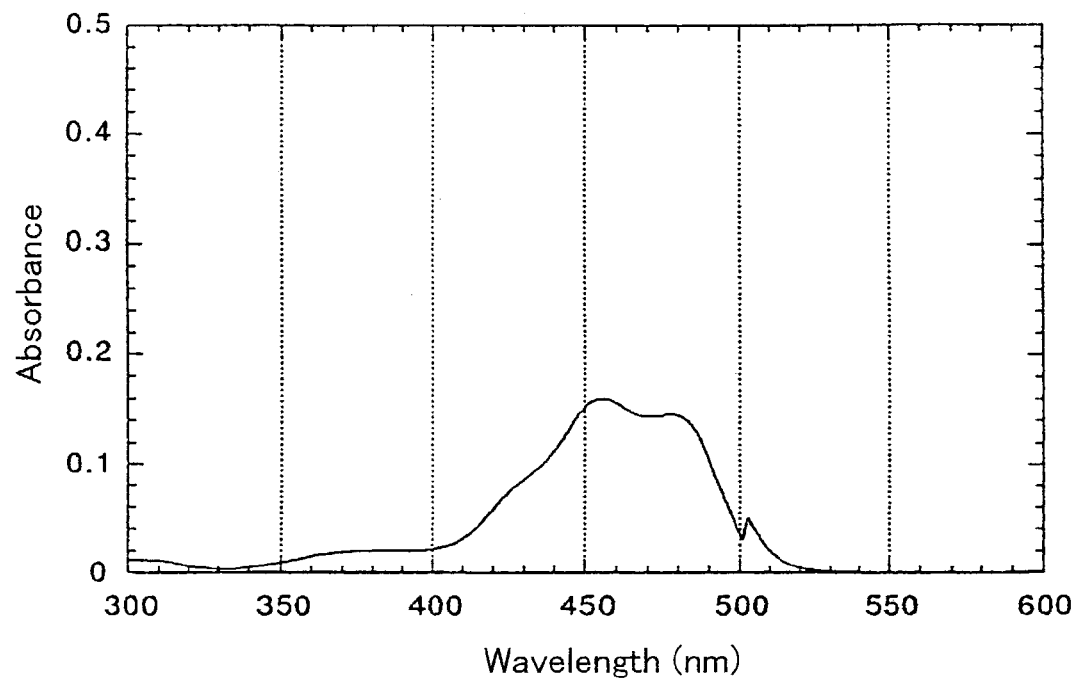
FIG. 5 shows an absorption spectrum of 10 µM compound (ss-3F) of the present invention dissolved in a sodium phosphate buffer (pH 7.4).
Figure 6:
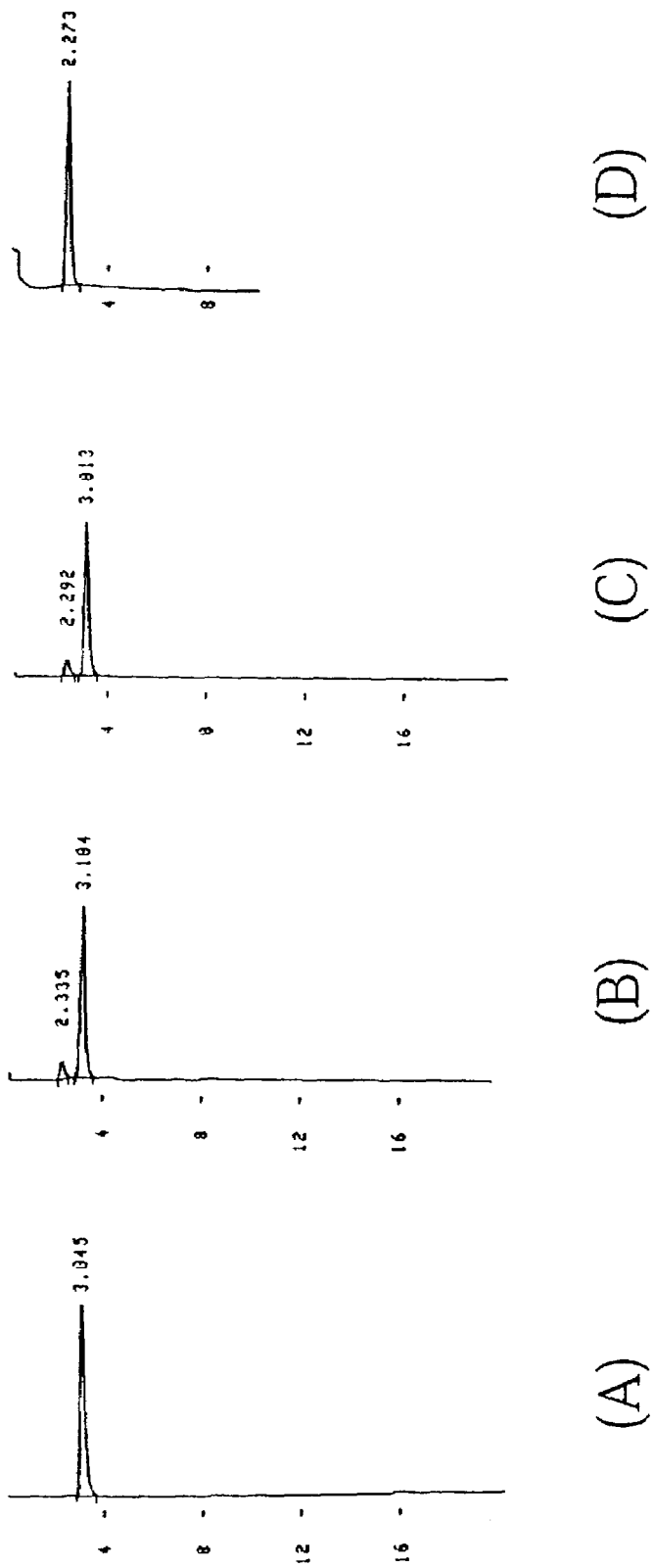
FIG. 6 shows a result of analysis by HPLC of a solution containing the compound (ss-3F) of the present invention obtained in Example 3. In the figure, indicated are results obtained from (A) a 10 µM ss-3F solution, (B) a reaction solution prepared by adding EP-1 to a 10 µM ss-3F solution to a final concentration of 5 mM, followed by reaction at 37° C. for 8 hours, (C) a solution prepared by adding hydrogen peroxide to a 10 µM ss-3F solution to a final concentration of 1 mM, adding ferrous perchlorate thereto to a final concentration of 500 µM, and then allowing to stand at room temperature for about 3 hours, and (D) a 1 µM fluorescein solution.

2) Absorption Spectrum ss-3F was dissolved in DMF at a concentration of 10 mM, and the solution was added with a 100 mM sodium phosphate buffer (pH 7.4) so as to give dissolution at a final concentration of 10 μM. The absorption spectrum of the resulting 10 μM ss-3F solution was measured. The results are shown in FIG. 5. It was verified that ss-3F had the absorption maximum at around 455 nm.

3) HPLC Spectrum

The solutions described below were analyzed by HPLC. The absorbance at 460 nm was measured using XTerra™RP$_{18}$ 5 μm (4.6×250 mm) as a column and an aqueous solution of acetonitrile/0.1M $NaHCO_3$=1/1 as an eluate with an elution rate of 1 ml/min.

(A) the 10 μM ss-3F solution
(B) a reaction solution prepared by adding EP-1 to the 10 μM ss-3F solution so as to give a final concentration of 5 mM and reacting at 37° C. for 8 hours
(C) a solution prepared by adding hydrogen peroxide to the 10 μM ss-3F solution so as to give a final concentration of 1 mM, and further adding ferrous perchlorate so as to give a final concentration of 500 μM, and then allowing to stand at room temperature for about 3 hours
(D) a 1 μM fluorescein solution A peak was detected at a retention time of 3.0 minutes for ss-3F alone (A). For a singlet oxygen generation system (B), a peak different from (A) was detected at 2.3 minutes, and for a hydroxyl radical generation system (C), a peak different from (A) was detected at 2.3 minutes. The peaks detected in (B) and (C) were congruent with a peak of fluorescein (D), i.e., 2.3 minutes. From these results, it was verified that ss-3F reacted with singlet oxygen or hydroxyl radical to generate fluorescein.

Example 5

1) Fluorescence Spectrum

Figure 7:
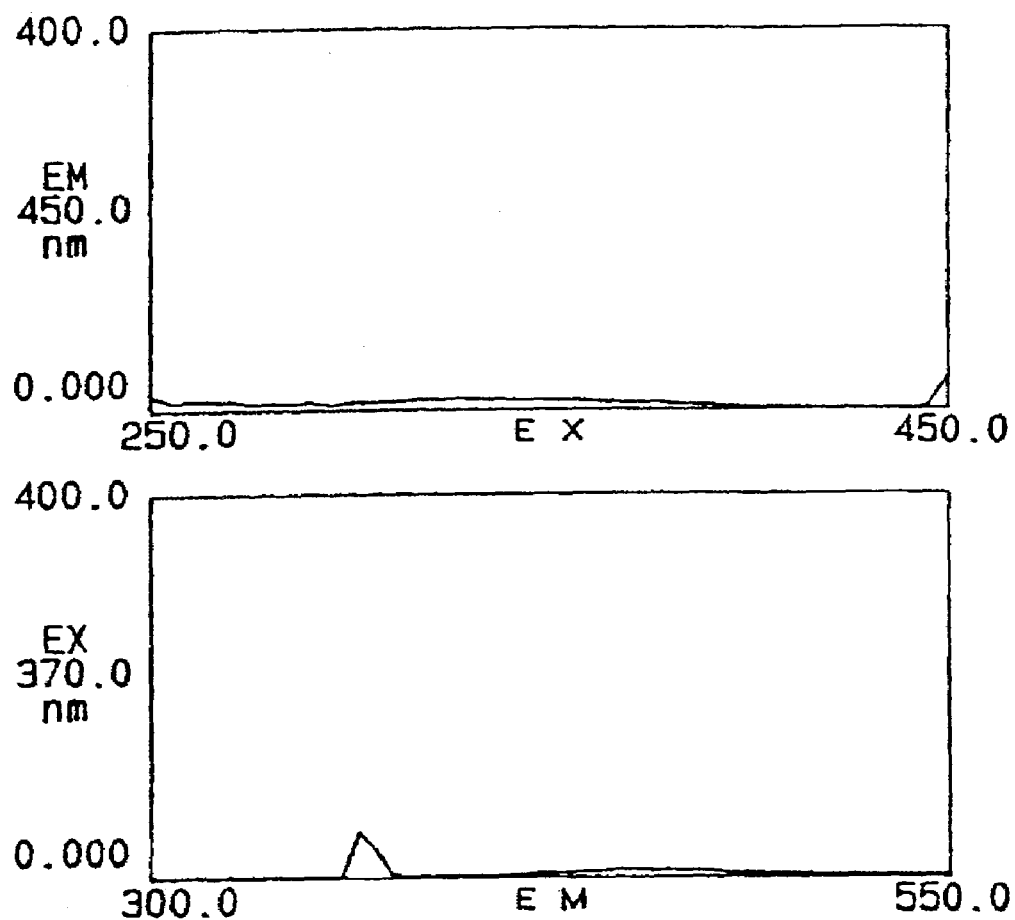
FIG. 7 shows an excitation spectrum and a fluorescence spectrum of a 10 µM solution of the compound (ss-3) of the present invention obtained in Example 1.
Figure 8:
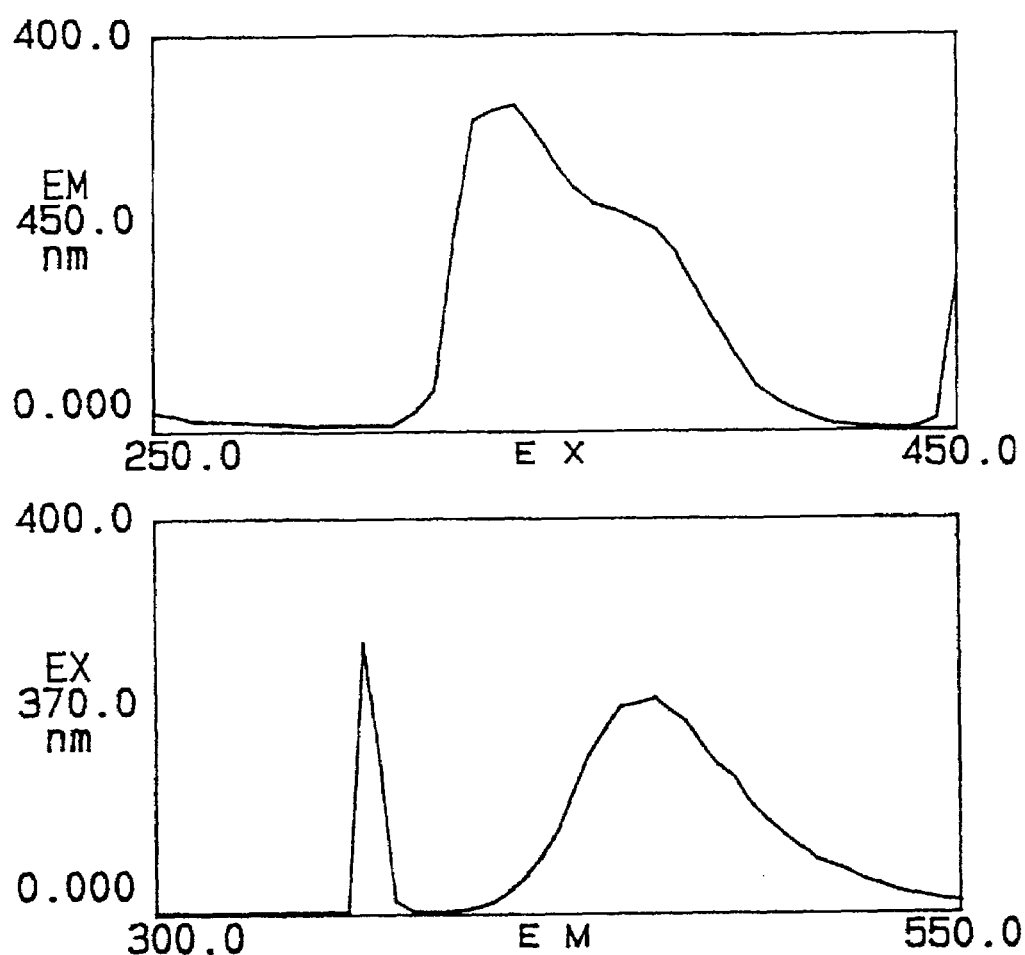
FIG. 8 shows an excitation spectrum and a fluorescence spectrum after the completion of the reaction between a 10 µM solution of the compound (ss-3) of the present invention obtained in Example 1 and singlet oxygen.

A fluorescence spectrum of ss-3 obtained in Example 1 was measured under the same conditions as those in 1) of Example 4, except that the excitation wavelength was at 370 nm and the fluorescence wavelength was at 450 nm. The result obtained in the absence of EP-1 was shown in FIG. 7, and the result of fluorescence spectrum of the solution after the completion of the reaction with EP-1 was shown in FIG. 8. As shown in FIGS. 7 and 8, ss-3 itself is substantially non-fluorescent, but emits fluorescence upon reaction with singlet oxygen.

Example 6

Comparison of Reactivity (Specificity) with Different Reactive Oxygen Species

The compounds of the present invention, ss-1F, and ss-3F were tested. DCFH (2',7'-dichlorodihydrofluorescein) was used as a control which was produced by hydrolyzing DCFH-DA (2',7'-dichlorodihydrofluorescein diacetate; Molecular Probes, D-399) as a commercially available agent for detecting reactive oxygen species. DCFH-DA was hydrolyzed in accordance with the method by Hempel et al. (Stephen L. Hempel et al., Free Radical Biology & Medicine, 27, 146–159, 1999) under an alkali condition to obtain DCFH. More specifically, DCFH-DA was treated with an aqueous solution of sodium hydroxide (pH 12) in the dark for 30 minutes, followed by immediate dilution with a 100 mM sodium phosphate buffer (pH 7.4) so as to give a concentration of 10 μM. The 10 μM DCFH solution was used for the test immediately after the preparation. A 10 μM solution was prepared for each of ss-1F and ss-3F using a 100 mM sodium phosphate buffer (pH 7.4) and used in the experiment. Each of ss-1F, ss-3F, and DCFH was treated under conditions "a" to "f" for 30 minutes (2 hours and 30 minutes only for "f") and changes in fluorescence intensity between before and after treatment were measured. The fluorescence intensity was measured under the same conditions as those in Example 4. Each concentration of the fluorescence probe was 10 μM (a 100 mM sodium phosphate buffer, pH 7.4). The results are shown in Table 1.

TABLE 1

| Reactive oxygen species | ss-1F | ss-3F | DCFH |
|---|---|---|---|
| Hydroxyl radical[a] | $3.3 \times 10^2$ | $6.0 \times 10^2$ | $4.8 \times 10^3$ |
| Singlet oxygen[b] | 4.8 | 8.7 | 26 |
| Superoxide[c] | 8.3 | 5.6 | 67 |
| Hydrogen peroxide[d] | 1.8 | <1.0 | $1.9 \times 10^2$ |
| Nitrogen monoxide[e] | 6.0 | <1.0 | $1.5 \times 10^2$ |
| Autoxidation[f] | <1.0 | <1.0 | $1.6 \times 10^3$ |

[a]Iron(II) perchlorate (100 μM) and hydrogen peroxide (1 mM) were added.
[b]EP-1 (100 μM) was added.
[c]$KO_2$ (100 μM) was added.
[d]Hydrogen peroxide (1 mM) was added.
[e]NOC13 (100 μM) was added.
[f]Allowed to stand just under a fluorescent lamp for 2 hours and 30 minutes.

DCFH successfully reacted with hydroxyl radical (condition "a") as well as other reactive oxygen species. The reactivity to autoxidation (condition "f") was also high, which occurrence is fundamentally undesirable. In contrast, ss-1F and ss-3F were completely free from autoxidation (condition "f") and had high reactivity to hydroxyl radical.

Example 7

Specific Detection of Peroxidase Activity

Figure 9:
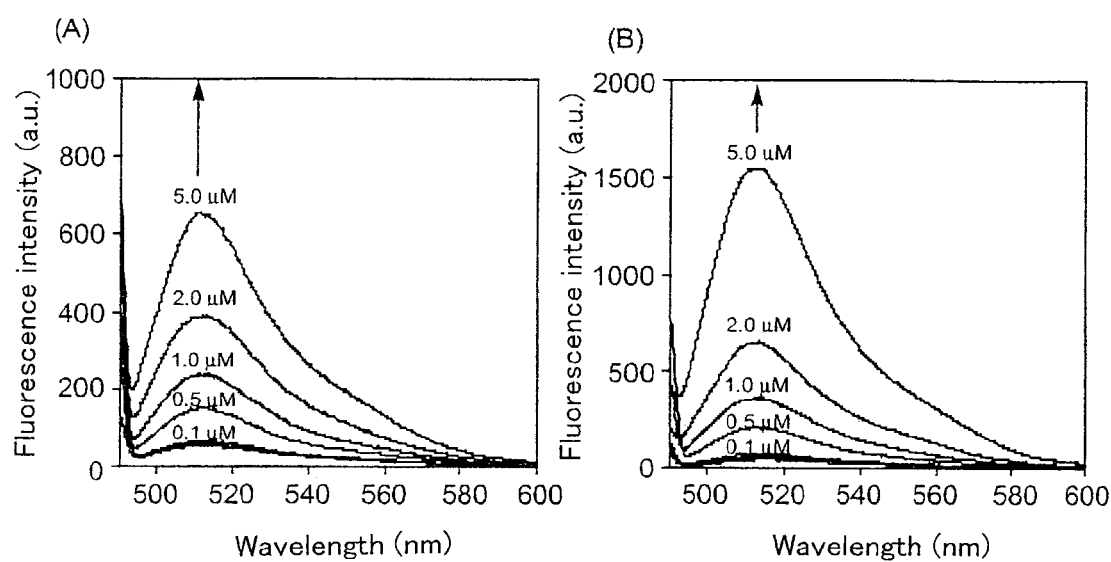
FIG. 9 shows the result of examination of reactivity between the compounds of the present invention (ss-1F and ss-3F) and $HRP/H_2O_2$. In the figure, indicated are results obtained from (A) ss-1F and (B) ss-3F. Numerical values in the figure represent $H_2O_2$ concentrations.

The compound of the present invention, ss-1F or ss-3F, was dissolved in DMF at a concentration of 10 mM, and the solution was added with a 100 mM sodium phosphate buffer (pH 7.4) so as to become dissolution at a final concentration of 10 μM. A 100 mM phosphate buffer (pH 7.4) of horseradish peroxidase was added to the resulting solution of ss-1F or ss-3F to a final concentration of 0.2 μM, and then hydrogen peroxide was added to final concentrations of 0, 0.01, 0.05, 0.1, 0.5, 1.0, 2.0, and 5.0 μM, and the fluorescence spectrum was immediately measured. The fluorescence spectrum was measured under the same conditions as those in 1) of Example 4, except that the fluorescence wavelength was at 515 nm. The results were shown in FIG. 9. As clearly shown in FIG. 9, both of ss-1F and ss-3F gave increase in fluorescence intensity in a concentration-dependent manner in the hydrogen peroxide concentration range of between 0 and 5.0 μM.

It is already verified from the result of Example 6 that ss-1F and ss-3F do not react with hydrogen peroxide, per se, and they suffer from no autoxidation. Accordingly, the result of Example 7 verified that the compound of the present invention enables specific and sole measurement of peroxidase activity.

INDUSTRIAL APPLICABILITY

The compound of the present invention is useful as an agent for measurement of reactive oxygens such as hydroxyl radical and singlet oxygen. The agent for measurement of reactive oxygens comprising the compound of the present invention and a method for measurement of reactive oxygens using said compound are particularly useful for measurement of reactive oxygens that are localized in particular class of cells or tissues in a living organism accurately and conveniently by using a bioimaging technique.

What is claimed is:

1. A compound represented by general formula (I) or (II) or a salt thereof:

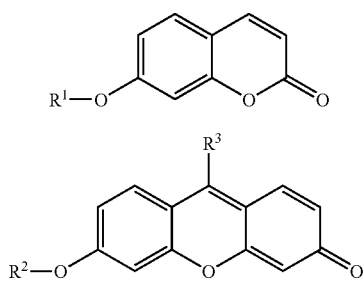

wherein $R^1$ and $R^2$ independently represent an aryl group which may be substituted and $R^3$ represents a 2-carboxyphenyl group which may be substituted.

2. The compound or a salt thereof according to claim 1, wherein $R^1$ and $R^2$ represent a phenyl group substituted with an amino group or a hydroxy group.

3. The compound or a salt thereof according to claim 1, wherein $R^3$ is a 2-carboxyphenyl group.

4. An agent for measurement of a reactive oxygen which comprises the compound according to claim 1 or a salt thereof.

5. A method for measurement of a reactive oxygen, which comprises the steps of:
   (A) reacting the compound according to claim 1 or a salt thereof with a reactive oxygen; and
   (B) measuring fluorescence of a dearylated compound or a salt thereof generated in the above step (A).

6. A method for measurement of an enzymatic activity of an enzyme, in which a reactive oxygen involves in said enzymatic activity, by using the compound according to claim 1 or a salt thereof.

7. The method according to claim 6, wherein the enzyme is a peroxidase.

8. An agent for measurement of an enzymatic activity of an enzyme, in which a reactive oxygen involves in said enzymatic activity, which comprises the compound according to claim 1 or a salt thereof.

9. The agent according to claim 8, wherein the enzyme is a peroxidase.

10. The compound or a salt thereof according to claim 2, wherein $R^3$ is a 2-carboxyphenyl group.

11. An agent for measurement of a reactive oxygen which comprises the compound according to claim 2 or a salt thereof.

12. An agent for measurement of a reactive oxygen which comprises the compound according to claim 3 or a salt thereof.

13. A method for measurement of a reactive oxygen, which comprises the steps of:
    (A) reacting the compound according to claim 2 or a salt thereof with a reactive oxygen; and
    (B) measuring fluorescence of a dearylated compound or a salt thereof generated in the above step (A).

14. A method for measurement of a reactive oxygen, which comprises the steps of:
    (A) reacting the compound according to claim 3 or a salt thereof with a reactive oxygen; and
    (B) measuring fluorescence of a dearylated compound or a salt thereof generated in the above step (A).

15. A method for measurement of an enzymatic activity of an enzyme, in which a reactive oxygen involves in said enzymatic activity, by using the compound according to claim 2 or a salt thereof.

16. A method for measurement of an enzymatic activity of an enzyme, in which a reactive oxygen involves in said enzymatic activity, by using the compound according to claim 3 or a salt thereof.

17. An agent for measurement of an enzymatic activity of an enzyme, in which a reactive oxygen involves in said enzymatic activity, which comprises the compound according to claim 2 or a salt thereof.

18. An agent for measurement of an enzymatic activity of an enzyme, in which a reactive oxygen involves in said enzymatic activity, which comprises the compound according to claim 3 or a salt thereof.

* * * * *